United States Patent
Inuzuka et al.

(10) Patent No.: US 6,186,998 B1
(45) Date of Patent: Feb. 13, 2001

(54) BAG FOR INFUSION SOLUTION AND METHOD OF MANUFACTURING SAME

(75) Inventors: Takeshi Inuzuka; Susumu Niwa, both of Tokyo-to (JP)

(73) Assignee: Hosokawa Yoko Co., Ltd., Tokyo-to (JP)

( * ) Notice: Under 35 U.S.C. 154(b), the term of this patent shall be extended for 0 days.

(21) Appl. No.: 09/086,602

(22) Filed: May 29, 1998

(30) Foreign Application Priority Data

Dec. 9, 1997 (JP) .................................................... 9-339048

(51) Int. Cl.$^7$ .............................. A61B 19/00; B65D 25/08
(52) U.S. Cl. .............................. 604/410; 604/89; 206/219; 383/38
(58) Field of Search ...................................... 604/408, 410, 604/416, 87, 89; 383/38–40, 207–211, 94; 206/219

(56) References Cited

U.S. PATENT DOCUMENTS

| 3,074,544 | 1/1963 | Bollmeier et al. . |
| 3,257,072 | * 6/1966 | Reynolds . |
| 3,692,493 | * 9/1972 | Teraski . |
| 3,708,106 | * 1/1973 | Sargent . |
| 3,749,620 | 7/1973 | Montgomery . |
| 4,608,043 | * 8/1986 | Larkin ..................................... 604/87 |
| 5,209,347 | * 5/1993 | Fabisiewicz et al. ................. 206/219 |
| 5,423,421 | * 6/1995 | Inoue et al. ........................... 206/219 |
| 5,474,818 | * 12/1995 | Ulrich et al. .......................... 383/107 |
| 5,706,937 | * 1/1998 | Futagawa et al. .................... 206/221 |
| 5,865,309 | * 2/1999 | Futagawa et al. .................... 206/219 |
| 5,944,709 | * 8/1999 | Barney et al. ........................ 604/410 |

FOREIGN PATENT DOCUMENTS

| 1 258 379 | 7/1961 | (FR) . |
| WO 97/37628 | 10/1997 | (WO) . |

* cited by examiner

Primary Examiner—John G. Weiss
Assistant Examiner—David J. Cho
(74) Attorney, Agent, or Firm—Young & Thompson (57) ABSTRACT

A bag for an infusion solution has front and back wall portions each formed of a flexible plastic film and provided with a plurality of chambers which are filled with one infusion solution and another infusion solution or medicament, independently. The chambers are sectioned by a boundary portion having at least one weak seal portion which is closed by separably bonding inside surfaces of the plastic films mutually facing at the boundary portion so that the one infusion solution and the another infusion solution or medicament in the respective chambers are mixed together when the weak seal portion is opened. The weak seal portion is formed by applying a separable coating material, which provides a reduced bonding strength in a heat sealing process, on one or both inside surfaces of the plastic films mutually facing at the boundary portion and then effecting heat sealing process to the boundary portion. The separable coating material is applied in a form of a dot-pattern through a printing process.

3 Claims, 7 Drawing Sheets

BAG FOR INFUSION SOLUTION AND METHOD OF MANUFACTURING SAME

BACKGROUND OF THE INVENTION

The present invention relates to a bag for an infusion solution particularly having a structure capable of easily mixing, at a time of use, an infusion solution with another infusion solution or a medicament other than the infusion solution which have been preliminarily independently sealed in the bag and also relates to a method of manufacturing such infusion solution bag.

In a case where it is required to prescribe an infusion solution, it has often be performed to prescribe a solution which has been prepared by mixing more than two kinds of infusion solutions or to prescribe a solution which was prepared by mixing a medicament solution other than the infusion solution with the infusion solution or dissolving powder of a medicament into the infusion solution. However, when the solution prepared by mixing the infusion solution with another infusion solution or medicament and the mixed solution is preserved, there is a fear such that the mixed solution may be denatured or discolored. Because of this reason, it is necessary to preliminarily preserve these solutions or medicaments as they are and mix them just before the prescription thereof. For example, with a dialysis solution utilized for peritoneal dialysis, it is difficult to preserve it for a long time if a pH thereof be not adjusted to weak acid, but it gives strong stimulus to a human organism in a case where it has not the neutral pH. Accordingly, it is necessary to add an alkali solution to the dialysis solution just before the prescription to make the pH thereof neutral. For example, in a case where a mixture solution of glucose infusion solution and amino acid infusion solution has been left as it is for a long time, Maillard reaction will be caused and the mixture solution will be discolored. In this example, it is also necessary to mix these solutions just before the prescription.

In view of the above matters, there has been provided an infusion solution bag having an inner space which is divided into a plurality of small chambers or sections into which infusion solutions, or infusion solution and a medicament other than the infusion solution, are accommodated respectively. These small chambers are sectioned by boundary portions which are sealed to be openable. These infusion solutions or medicament solutions stored in the respective chambers can be mixed together by opening the boundary portions just before the use.

In one type infusion solution bag of conventional structure, a shell portion of the infusion solution bag is pinched from the outer side thereof at several portions by using pinching members to divide the inner space of the bag into a plurality of small chambers or sections and various infusion solutions or the like are accommodated into these divided sections respectively. The pinching members are removed at the time of prescription to mix these infusion solutions together.

In another type of conventional structure, opposing film materials constituting both surfaces of an infusion solution bag are closed, through a heat sealing process, at boundary portions by which the inner space of the infusion solution bag is divided into a plurality of small sections. A port forming member is mounted to a part of each boundary portion, infusion solutions or other medicament solutions are accommodated in the small sections respectively, and these solutions are mixed at the infusion solution prescription time by breaking, for example, bending, the port forming member.

However, according to the conventional structures mentioned above, it is necessary to preliminarily prepare pinching members or port forming members and attach them to the infusion solution bag, resulting in increasing of troublesome working and increasing of manufacturing cost. Furthermore, it is difficult to strictly section the respective small chambers in desired shapes, and moreover, in the case of using the port forming member, since the thus formed port has a small opened area, it takes much time to complete the mixing of the infusion solutions accommodated in the respective sections.

Still furthermore, prior art provides a method in which opposing film materials, constituting both surfaces of an infusion solution bag, are closed, through a heat sealing process, with a resin film being interposed therebetween for weakening a sealing strength, at boundary portions by which the inner space of the infusion solution bag is divided into a plurality of small sections. Infusion solutions or other medicament solutions are accommodated into these small sections or chambers, and when it is required to mix these solutions in the respective small sections together, the weakly sealed part of the boundary portion is separated by applying pressure to the bag body and, then, the solutions in the respective sections are mixed through the opened boundary portion.

However, in this conventional structure, it is also necessary to prepare a resin film formed of a relatively specific material having a weakened sealing strength and dispose such resin film to a desired position of the boundary portion sectioning the respective small chambers of the bag, also involving troublesome working and increasing the manufacturing cost. Furthermore, since it is difficult to arrange the resin film having the weakened strength in a desired pattern, it is also difficult to section the small chambers so as to provide desired shapes. Still furthermore, in this structure, it is necessary to select the material for the resin film for the adjustment of the sealing strength of the boundary portion to be separated and to suitably adjust the heating temperature and pressure at the sealing time. However, it is extremely difficult to finely adjust the sealing strength of the resin film by selecting the material therefor, and moreover, in the heat sealing process, it is difficult to stably control the sealing strength by adjusting the heating temperature and pressure, which may result in that the thus manufactured infusion solution bag has no uniform sealed strength at the boundary portions to be separated.

SUMMARY OF THE INVENTION

An object of the present invention is to substantially eliminate defects or drawbacks encountered in the prior art described above and to provide a bag for an infusion solution which has an inner space divided into a plurality of chambers or sections into which infusion solutions, or infusion solution and a medicament other than the infusion solution, are accommodated respectively, and these chambers are sectioned by weakly sealed portions which are openable, these chambers having optional shapes as occasion demands.

Another object of the present invention is to provide a method of effectively manufacturing an infusion solution bag, which has an inner space divided into a plurality of chambers or sections into which infusion solutions, or infusion solution and a medicament other than the infusion solution, are accommodated respectively, and these chambers are sectioned by weakly sealed portions which are openable, in a material saving manner with reduced working labor.

These and other objects can be achieved according to the present invention by providing, in one aspect, a bag for an infusion solution having front and back wall portions each formed of a flexible plastic film and provided with a plurality of chambers which are filled with one infusion solution and another infusion solution or medicament, independently, the chambers being sectioned by a boundary portion having at least one weak seal portion which is closed by separably bonding inside surfaces of the plastic films mutually facing at the boundary portion so that the one infusion solution and the another infusion solution or medicament in the respective chambers are mixed together when the weak seal portion is opened, wherein the weak seal portion is formed by applying a separable coating material, which provides a reduced bonding strength in a heat sealing process, on one or both inside surfaces of the plastic films mutually facing at the boundary portion and then effecting heat sealing process to the boundary portion.

The separable coating material may contain at least one kind of silicone release agents. The boundary portion may have a seal portion hard to be opened other than the weak seal portion.

According to the structure of the infusion solution bag of the present invention, it is possible to form the weak seal portion in a relatively easy manner such that the separable coating material is applied on one or both inside surface of the plastic films forming the front and back wall of the bag respectively. Therefore, there is no need to provide a pinching member for pinching the infusion solution bag, a port forming member of a molded product or a resin film for weakening a sealing strength of the boundary portion between the chambers, and also no need to mount them on a predetermined position of the bag, thus forming the infusion solution bag with no trouble and labor.

Furthermore, according to the present invention, since the weak seal portion is formed by applying the separable coating material on the inside surface of the plastic film, the weak seal portion can be easily made into an optional pattern in comparison with the conventional openable portion provided with the pinching member, the port forming member, the resin film for weakening the sealing strength or the like. As a result, the small chambers can be formed so as to have optional shapes at desired positions, thus performing the mixing of the inner contents of the respective small chambers in a correct mixing order.

In preferred embodiments, the separable coating material is applied in a form of a dot-pattern. The sealing strength of the weak seal portions can be finely controlled by changing an area-proportion of the dots, thus adequately adjusting a separable performance of the weak seal portions. In addition, according to the adjustment by using the area-proportion of dots, the stable sealing strength can be always achieved and all the products have uniform sealing strength.

One chamber, which is filled with the infusion solution to be flowed out into another chamber adjacent to the one chamber by opening the weak seal portion formed between both the chambers, may have a portion protruded towards the weak seal portion. According to the present invention, the small chambers of the bag can be formed in an optional shape at a desired position, thus the chamber can be also formed in the protruded shape. As a result, it comes to provide the infusion solution bag capable of performing the mixing of the inner contents of the respective small chambers in a correct mixing order.

In another aspect of the present invention, to achieve the above mentioned objects, there is also provided a method of manufacturing an infusion solution bag which has front and back wall portions each formed of a flexible plastic film and which is provided with a plurality of chambers which are filled with one infusion solution and another infusion solution or medicament, independently, the chambers being sectioned by a boundary portion having at least one weak seal portion which is closed by separably bonding inside surfaces of the plastic films mutually facing at said boundary portion so that one infusion solution and the another infusion solution or medicament in the respective chambers are mixed together, the manufacturing method comprising the steps of:

preparing a flexible plastic film;

applying a separable coating material, which provides a reduced bonding strength in a heat sealing process, on one or both inside surfaces of the plastic films in an area forming the weak seal portion;

mating or folding the plastic film so as to form overlapped two portions forming the front and back wall portions of the infusion solution bag;

effecting heat sealing to an area forming peripheral edge portions of the infusion solution bag except portions at which filling ports are formed and effecting heat sealing to an area forming the boundary portion including the weak seal portion;

filling the one infusion solution and another infusion solution or medicament into the chambers, independently; and closing and sealing the filling ports.

In this aspect, the separable coating material may preferably be applied in a form of dot-pattern to be changeable in area ratio thereof for adjusting separability of the weak seal portion. The separable coating material is applied so as to provide a dot-pattern on the inner surface of the plastic film through a printing process. The separable coating material may contain at least one kind of silicone release agents.

According to the characters of the infusion solution bag manufacturing method of the present invention, the portions of the boundary portion other than the weak seal portion and the peripheral edge portion of the bag can be heat-sealed together with the weak seal portion, so that the infusion solution bag provided with small chambers can be effectively manufactured. Furthermore, since the separable coating material can be applied through the printing process to the weak seal portion at, the inside surface of the plastic film, the area-proportion of dots in the printing process can be easily adjusted as well as easy formation of the weak seal portion with optional pattern.

The nature and further characteristic features of the present invention will be made more clear from the following descriptions made with reference to the accompanying drawings.

DESCRIPTION OF THE PREFERRED EMBODIMENTS

Preferred embodiments of the present invention will be described hereunder more in detail with reference to the accompanying drawings.

Figure 1:
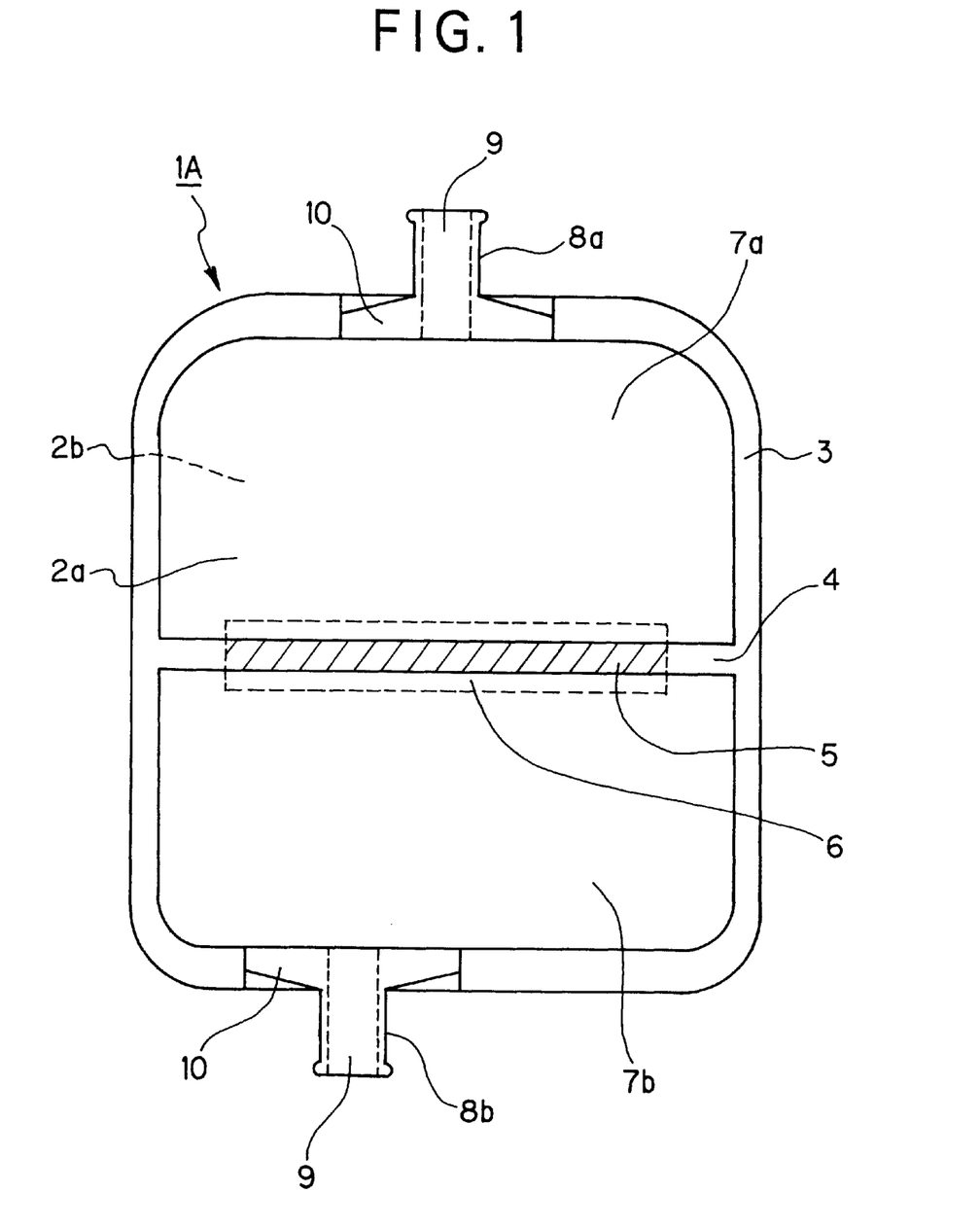
FIG. 1 is a front view of an infusion solution bag according to one embodiment of the present invention.

FIG. 1 is a front view of one embodiment of a bag for an infusion solution (infusion solution bag 1A) according to the present invention. The infusion solution bag 1A is one for artificial dialysis, which is prepared by overlapping two transparent flexible plastic films 2 (2a, 2b), and peripheral portions 3 thereof are heat sealed to thereby provide a bag having sealed four side peripheral portions, called hereinafter as four-side seal bag or merely seal bag.

Figure 2:
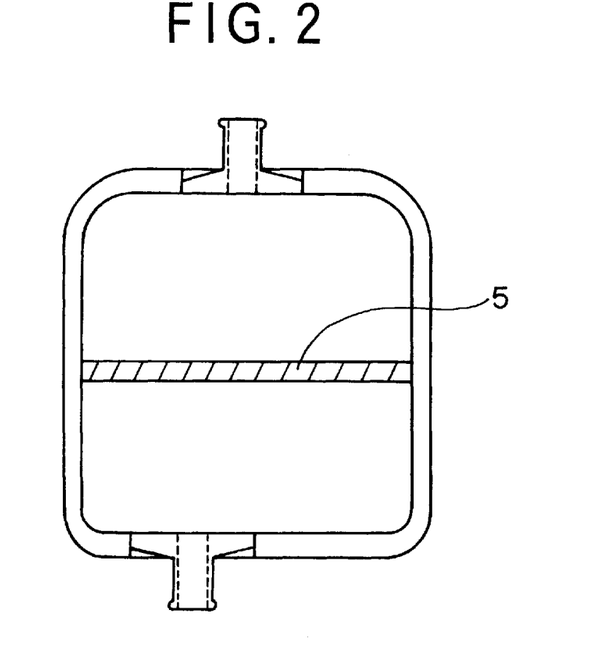
FIG. 2 is a front view of an infusion solution bag provided with one example of a weakly sealed portion.

The infusion solution bag 1A has an inner space which is divided into two small chambers or sections 7a and 7b by a boundary portion 4 crossing a shell portion of the bag 1A. A dialysis solution is accommodated in one 7a of small chambers and an alkaline solution is accommodated in the other one 7b thereof so as to make neutral the dialysis solution, these solutions being independently sealed. The boundary portion 4 is sealed and closed by heat sealing the opposing plastic films 2a and 2b constituting front and back wall portions (front and back surface portions) of the infusion solution bag 1A. The boundary portion 4 has both side end portions, near the peripheral sides of the bag, at which both the front and back wall portions 2a and 2b are firmly bonded. The boundary portion 4 also has a central portion 5 shown by oblique lines which is weakly bonded so as to be separable as a weakly sealed portion 5, which may be called herein merely as weak seal portion 5. As mentioned above, although the boundary portion 4 of the infusion solution bag 1A shown in FIG. 1 has a separable portion as the weak seal portion 5 and also has a firmly sealed portion not separated, the boundary portion 4 may be formed entirely as the weak seal portion 5 as shown in FIG. 2.

The separable weak seal portion 5 can be formed in a manner that a separable coating material such as silicone separable materials (release agents) is applied to either one of or both of inside surfaces of the plastic films 2a and 2b of the front and back wall portions of the bag 1A and then heat sealing process is performed to that portion to thereby form the weak seal portion 5. Accordingly, the weak seal portion 5 is constituted by an area formed by overlapping an area 6 of the plastic film to which the coating material is applied and the boundary portion 4 to which the heat sealing process is applied.

With the infusion solution bag 1A shown in FIG. 1, the separable coating material applied area 6 is set so as to have a width slightly larger than that of the boundary portion 4 for the purpose of easily positioning the area 6 and the boundary portion 4. However, it will be easily understood that it is preferable to set the width of the coating material applied area 6 equal to that of the boundary portion 4 for preventing the applied coating material from directly contacting to the infusion solution in the sectioned chambers of the bag 1A.

The separable coating material is applied to the weak seal portion 5 of the plastic film of the infusion solution bag 1A in a dot-pattern with a predetermined area-proportion of dots (dot percentage). According to the present invention, the bonding strength, i.e. Sealable performance, of the bonding surface of the weak seal portion 5 can be controlled by adjusting the area-proportion of dots of the coating material in a manner such that when the infusion solution bag 1A is not separated, for example, in a time of reserving the bag as it is, the sealed condition can be suitably maintained, whereas when either one of small chambers 7a or 7b is pressed with a pressure such as that easily applied by a weight of a user from outside of the bag, the weak seal portion 5 is easily separated and the infusion solutions or the like accommodated in both the chambers 7a and 7b are mixed.

Figure 3:
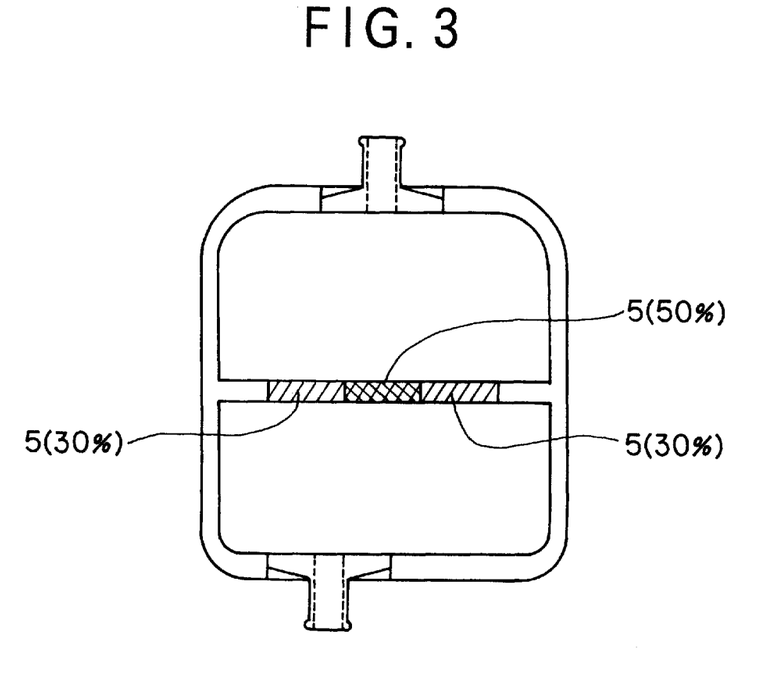
FIG. 3 is a front view of an infusion solution bag provided with another example of a weakly sealed portion.
Figure 4:
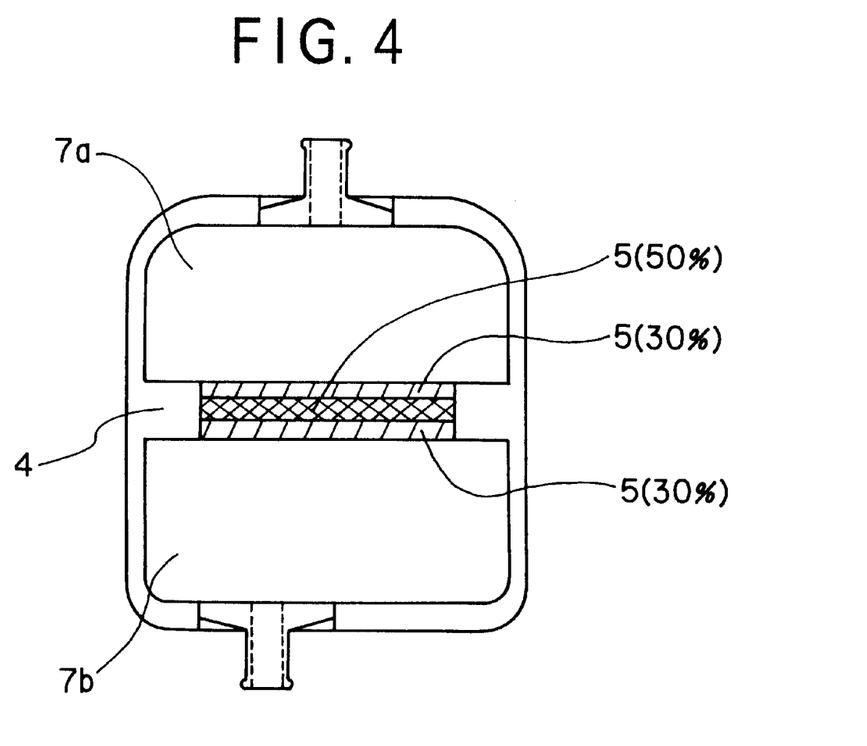
FIG. 4 is a front view of an infusion solution bag provided with a further example of a weakly sealed portion.
Figure 5:
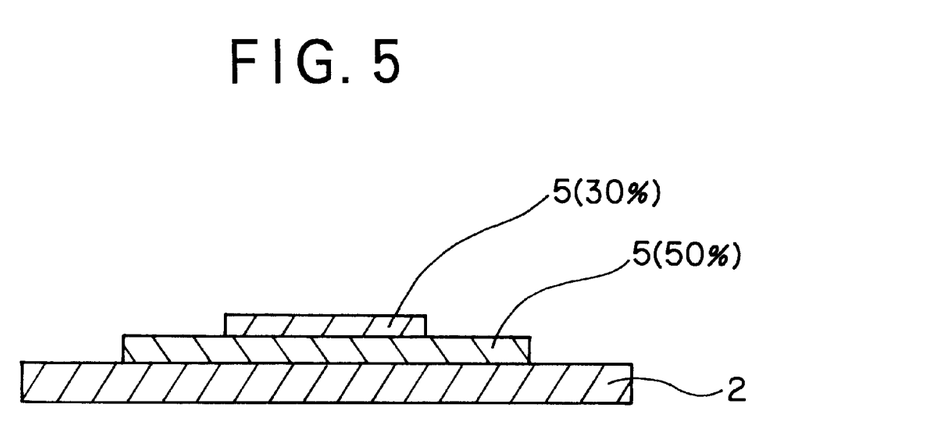
FIG. 5 is a sectional view of a still further example of a weakly sealed portion of the infusion solution bag.

Furthermore, it may be possible to partially change the separable performance of the weak seal portion by partially changing the area-proportion of dots thereof. For example, the area-proportion of dots at the central portion of the weak seal portion 5 may be higher than that at both the end portions thereof. In the example shown in FIG. 3, the area-proportion of dots at the central portion of the weak seal portion 5 is made to 50% and that of the end portion is made to 30%. In another example, the area-proportion of dots at both side edge portions of the weak seal portion 5 facing the small chambers of the bag may be made smaller than the other portion thereof and, in the example shown in FIG. 4, the area-proportion of dots at both the side edge portions of the weak seal portion 5 facing the small chambers 7a and 7b of the bag is made to 30% and that at the central portion between both the side edge portions is made to 50%. In a further example, a separable coating material is applied first to the entire portion of the weak seal portion 5 and, then, the separable coating material is additionally applied, in an overlapped manner, to a partial portion of the weak seal portion 5. In the example of FIG. 5, the separable coating material is entirely applied to the weak seal portion 5 on the plastic film 2 with the area-proportion of dots of 50% and is further partially applied thereto in the overlapped manner with the area-proportion of dots of 30%.

Furthermore, discharge members 8a and 8b made of plastic material are provided for the upper and lower end portions, as viewed in FIG. 1, for example, of the infusion solution bag 1A. The discharge members 8a and 8b have tip end portions to which flanged portions 10 are formed so as to extend bilateral directions, and these flanged portions 10 and the inner surface of the peripheral portion of the plastic film 2a or 2b are heat-sealed. The discharge members 8a and 8b are formed with inner flow passages 9 communicating the inner spaces of the chambers with a space outside the infusion solution bag 1A, and the flow passages 9 are closed by means of rubber plugs.

When a pressure is applied to the infusion solution bag 1A, the weak seal portion 5 thereof is separated and opened so that the infusion solutions or the like in the respective small chambers of the bag 1A are mixed together, and the mixed solution can be discharged outward by, for example, piercing a needle of an injector attached to one end of an instillation tube to the rubber plug applied to the discharge member 8a (8b) of the infusion solution bag 1A.

The infusion solution bag 1A of the structure mentioned above will be manufactured in the following manner.

Figure 6:
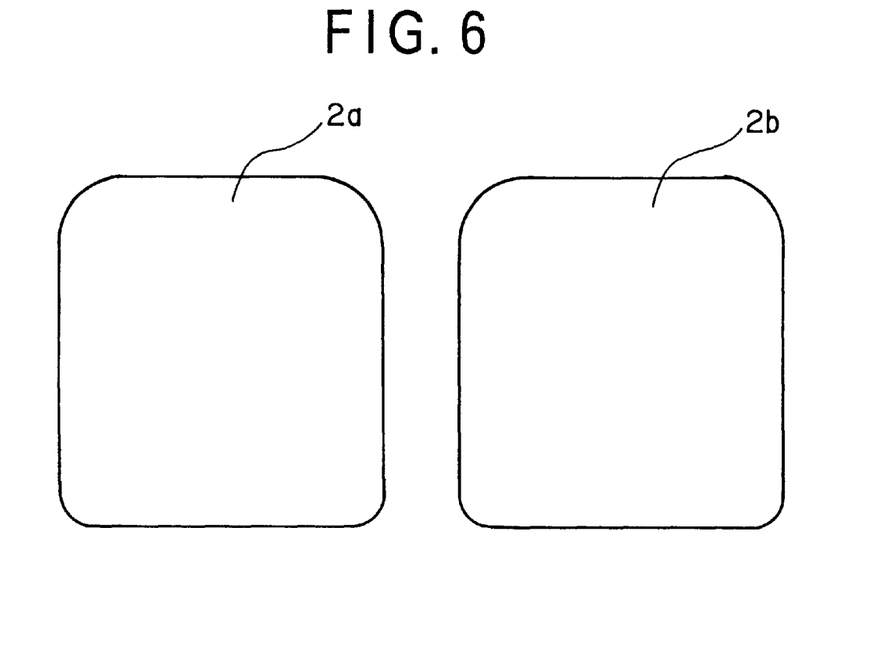
FIGS. 6 to 9 are views for explaining respective steps for a method of manufacturing an infusion solution bag according to the present invention, the steps being performed in this order of figures.

First, a flexible plastic film as a material for forming an infusion solution bag is cut, as shown in FIG. 6, to prepare plastic films 2a and 2b constituting front and back wall portions (front and back side surfaces) of the bag. There will be used, as a preferred material of such plastic film, flexible polypropylene (PP) film, plasticized polyvinyl chloride (PVC) film, flexible linear low density polyethylene (LLDPE) film, flexible ethylene vinyl acetate (EVA) copolymer film or the like. Further, a composite film formed by laminating a plurality of layers of different plastic materials may be used as a material for an infusion solution bag. It is desired for such film to have a thickness of about 200 to 500 μm. As occasion demands, a heat seal layer may be additionally formed to an inside surface of the plastic film, particularly, at portions constituting the peripheral edge portion and the boundary portion of the infusion solution bag by coating a heat seal material to these portions.

Figure 7:
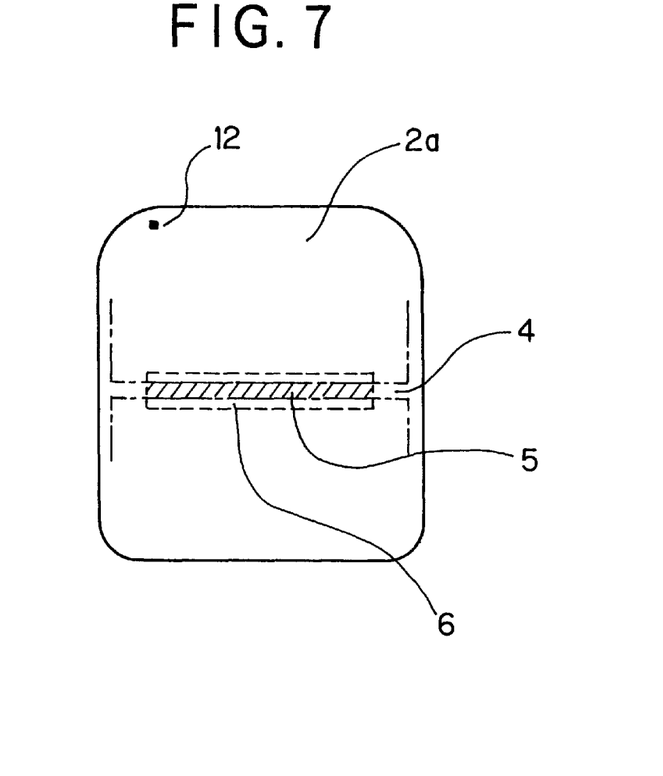

Next, with reference to FIG. 7, a separable coating material is applied to the area, constituting the weak seal portion 5, shown with oblique lines in FIG. 7, of the inside surface of the plastic film 2a as the front wall portion of the bag. In usual, a positioning mark 12 is applied to an inconspicuous portion of the plastic film and the separable coating material is then applied to the predetermined portion with reference to this mark 12. Although the coating method is not specifically defined, a print coating method may be most preferred in various coating methods for the reason that the print coating method is most suitable for coating the material in optional pattern.

It is to be noted that it is required for the separable coating material to have a property for suppressing a bonding strength of the heat-sealed bonded surface and also have a heat-resisting property and a safeness for a human body. In this aspect, as the separable coating material, there will be used various hardenable type coating agents included in silicones, polyvinyl chloride compounds, epoxy compounds, polyesters, or the like materials. Among these materials, the hardenable type silicone separable agents (release agents) will be most suitable in the viewpoint of safeness. Although the hardenable type silicone separable agent is used as a release agent which is coated to a release paper of a tack label or adhesion tape, it is necessary for the separable agent for the present invention to have safeness property for the human body. In this viewpoint, one desired coating material for the present invention will be a silicone release agent which can be hardened by the use of platinum catalyst. Standards or references of materials for medical use are different in respective countries, and in Japan, it is necessary for the separable coating material to pass test required for plastic containers for infusion solutions on the basis of the Japanese Pharmacopoeia.

The easily separable coating material may be applied to an area 6 (enclosed with dotted lines in FIG. 7) which has a width slightly wider than that of an area (shown with one-dot-chain line in FIG. 7) constituting the boundary portion 4. When the easily separable coating material is applied to such wide area 6, the positional alignment between this area 6 and the area constituting the boundary portion 4 can be easily performed. However, it is more preferable to coat the separable coating material with the same width as that of the area constituting the boundary portion 4 for the reason that when the coating material is applied with the same width, the infusion solution in the bag does not contact the applied separable coating material. Further, the separable coating material may be applied to the inside surface of the plastic film 2b of the back wall portion forming the weak seal portion as well as the inside surface of the plastic film 2a of the front wall portion.

Figure 8:
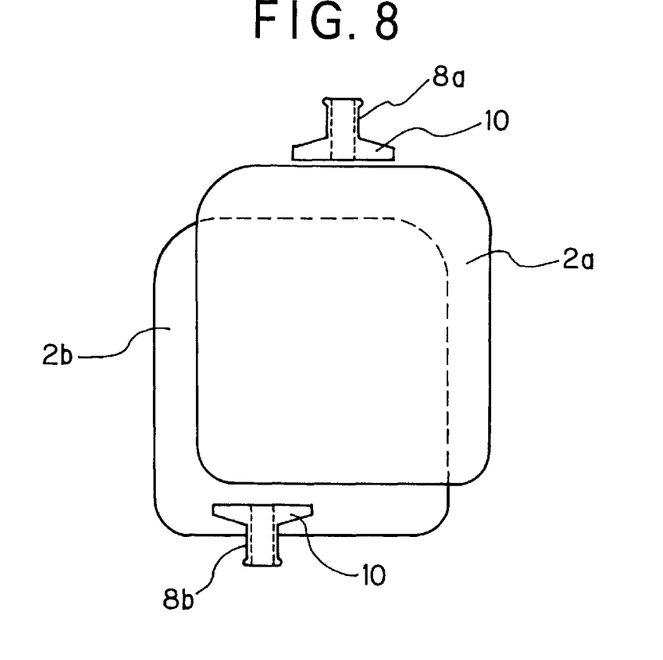

In a further process, as shown in FIG. 8, both the plastic films 2a and 2b are overlapped so that the inside surfaces thereof face each other, and then, the discharge members 8a and 8b are provided to the predetermined positions so that the flanged portions 10 of these discharge members 8a and 8b are interposed between the plastic films 2a and 2b. Further, a single sheet of plastic film may be used as the plastic films 2a and 2b, and in this case, the single plastic film sheet is folded at the central portion thereof so as to form the front wall side plastic film 2a and the back wall side plastic film 2b.

Figure 9:
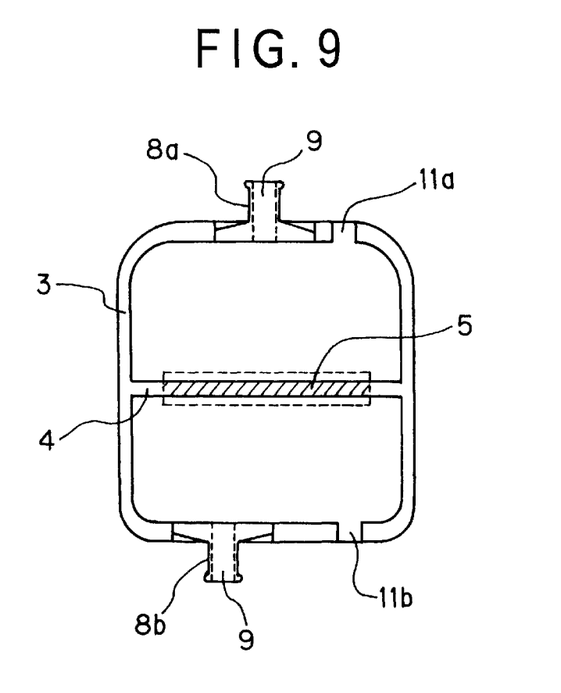

In a further succeeding process, as shown in FIG. 9, the areas constituting the peripheral edge portions 3 and the boundary portion 4 of the infusion solution bag 1A are heat-sealed, and at this process, as to the area constituting the boundary portion 4, all the portions including the weak seal portion 5 and the other portions are heat-sealed. Further, at this time, since the filling of the infusion solution has not been completed, it will be desired that the areas constituting the peripheral edge portions 3 and the boundary portion 4 remain unsealed partially, i.e. one portion to each area, without heating so as to provide infusion solution filling ports 11a and 11b. However, in a case where the infusion solution is fed into the bag 1A through the discharge members 8a and 8b, it is not necessary for the unsealed portion to remain because the infusion filling ports can be automatically formed by mounting the discharge members 8a and 8b to the infusion solution bag 1A. As the heat sealing method, in the present invention, a bar-seal method, a high-frequency seal method, an ultrasonic-seal method or other known heat seal methods will be utilized.

Thereafter, the infusion solutions or other substances are filled up in the respective small chambers. In this time, it is necessary to fill at least one of the small chambers with the infusion solution and it may be possible to fill the other small chamber with a medicament such as powder medicament or a little amount of medicament solution other than the infusion solution. However, when the medicament other than the infusion solution is utilized, a little amount thereof is generally used, so that the other small chamber will have a relatively small volume. After the filling of the infusion solutions or the like, the filling ports 11a and 11b are heat-sealed and the flow passages 9 of the discharge members 8a and 8b are closed by means of rubber plug. A retort sterilization or other treatment will be performed as occasion demands. The infusion solution bag 1A such as shown in FIG. 1 can be manufactured by performing the above-mentioned processes.

The bonding strength of the plastic film 2a forming the front wall portion and the plastic film 2b forming the back wall portion at the weak seal portion 5 can be adjusted by selecting the separable coating materials or changing the heat-sealing temperature or heat-seal pressure, and preferably, it is desired to apply the easily separable coating material in dot-shape pattern while changing the area-proportion of the dots, thus performing the fine adjustment. Furthermore, according to the adjustment by using the area-proportion of dots, the stable sealing strength can be always achieved and all the products have uniform sealing strength. The easily separable coating material can be easily printed in the dot-pattern by the printing method and, in this method, the area-proportion of dots can be optionally changed.

Figure 10:
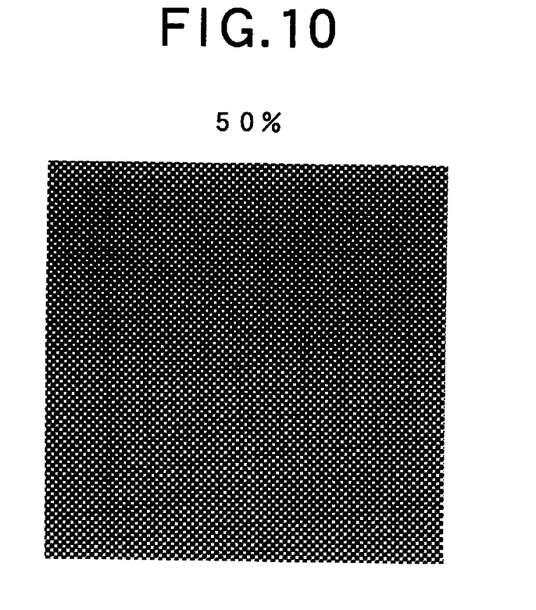
FIG. 10 is a view showing 50% area-proportion of dots (dot-pattern area ratio (%))
Figure 11:
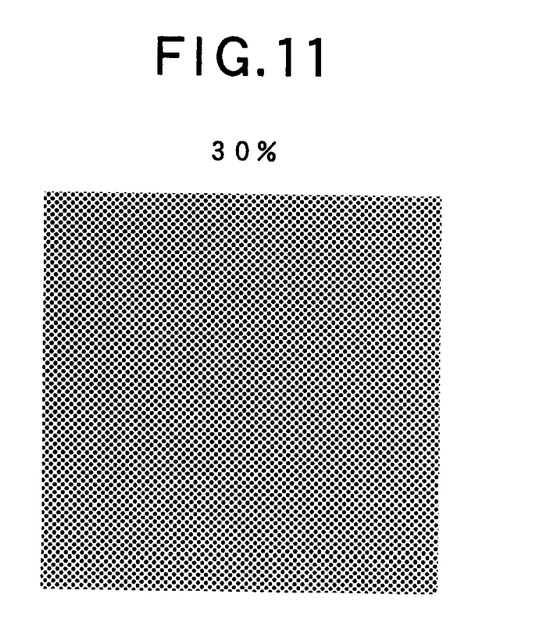
FIG. 11 is a view showing 30% area-proportion of dots (dot-pattern area ratio (%))

In one experimental example, two films of polypropylenes each having a thickness of 300 μm were overlapped and then heat-sealed at a heating temperature of 210° C. with a sealing pressure of 2 kg/cm$^2$ for 3 seconds, thus forming a test piece having a width of 15 mm. When such overlapped plastic films were separated, the sealing strength was about 5.1 kg/15 mm (width). On the contrary, a hardenable-type separable agent of silicones was applied to the inside surface of one of the same polypropylene films in the dot-pattern having an area-proportion of dots of 50% as shown in FIG. 10 through the printing method and then heat-sealed with the same conditions mentioned above. In this case, the sealing strength was adjusted to about 1.4 kg/15 mm (width). Furthermore, in the same manner, when the hardenable-type separable agent of silicones was applied to the inside surface of the other one of the polypropylene films in the dot-pattern having an area-proportion of dots of 30% as shown in FIG. 11 through the printing method and then heat-sealed with the same conditions mentioned above. In this case, the sealing strength was adjusted to about 2.7 kg/15 mm (width).

The suitable sealing strength of the weak seal portion to be determined differs in accordance with the differences of the amounts of the inner contents of the infusion solution bag, the kind of users such as man or woman, or other conditions. According to the infusion solution bag of the present invention, the sealing strength can be finely and optionally adjusted by changing or adjusting the area-proportion of dots.

In a case where the mixing order of the infusion solutions or the like in the respective chambers is not so important, the infusion solution bag will be formed to have a general structure provided with a linear weak seal portion such as shown in FIG. 1. However, in a case where the infusion solutions or the other medicament in the chambers have a combination having a fear of being denatured or discolored if the mixing order thereof is not correctly carried out and, hence, in a case where it is necessary to carry out the mixing thereof with the predetermined order, it is required for the infusion solution bag to be formed with the small chambers having shapes or positions suitable for carrying out the correct mixing order of the inner contents. According to the present invention, since the weak seal portion is formed by applying the separable coating material on the inside surface of the plastic film, the boundary portion including such weak seal portion can be formed so as to have an optional pattern, and accordingly, small chambers each having an optional shape can be easily formed to an optional position. Furthermore, according to the printing method such as gravure printing method, the separable coating material can be particularly easily applied in the desired pattern shape.

Figure 12:
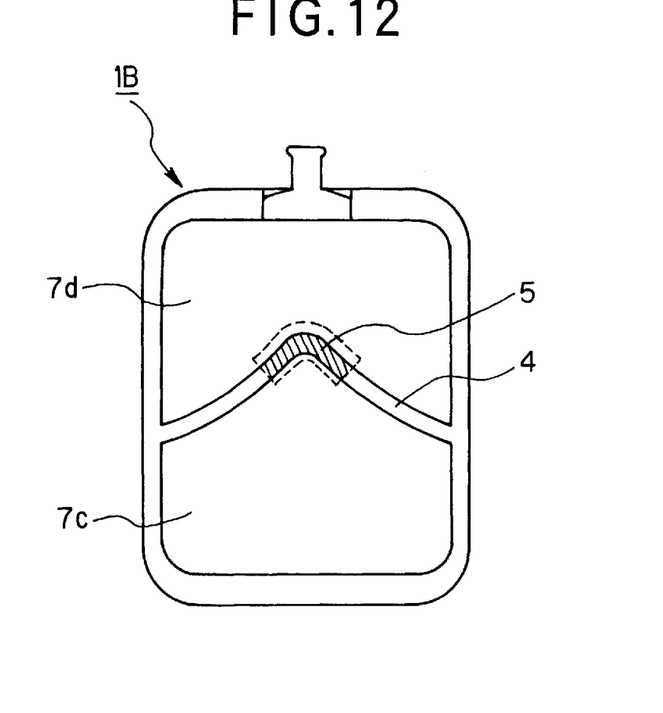
FIG. 12 is a front view of an infusion solution bag having two chambers according to another embodiment of the present invention in which mixing order is specified.

FIG. 12 shows another example of an infusion solution bag 1B of the present invention. In this infusion solution bag 1B, the boundary portion 4 has a central portion protruded towards a small chamber side 7d so as to provide a V-shape in a manner such that the inner space of a small chamber 7c is narrowed towards the weak seal portion 5 formed between the small chambers 7c and 7d. According to this structure, when the small chambers 7c of the infusion solution bag 1B is pressed, the inner pressure applied to the small chamber 7c is concentrated to the narrowed central portion thereof, i.e. toward the weak seal portion 5, and therefore, when the weak seal portion 5 is separated and opened, the infusion solution in the small chamber 7c flows into the other small chamber 7d. On the contrary, according to the structure of FIG. 12, if the small chamber 7d is erroneously pressed, the inner pressure is hardly concentrated to the central portion thereof, i.e. the weak seal portion 5, so that the weak seal portion 5 will be hard to be separated and opened, and hence, the flow of the infusion solution from the small chamber 7d to the small chamber 7c will be hardly caused.

Figure 13:
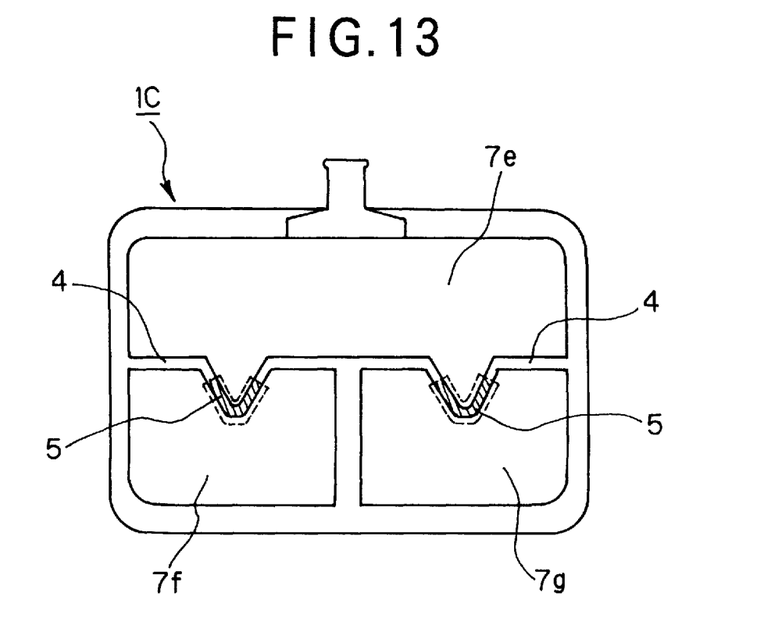
FIG. 13 is a front view of an infusion solution bag having three chambers according to a modification of FIG. 12 of the present invention in which mixing order is specified.

FIG. 13 shows a further example of an infusion solution bag 1C of the present invention provided with three small chambers 7e, 7f and 7g into which different three kinds of infusion solutions are accommodated. In this infusion solution bag 1C, the boundary portions 4 between the small chamber 7e and the small chambers 7f and 7g have central portions narrowed, i.e. protruded, towards the small chamber side so as to provide a V-shape in the manner similar to that mentioned above. According to this structure, the small chamber 7e is first pressed so as to mix the infusion solution therein with the infusion solution contained in the small chamber 7f by flowing the infusion solution in the small chamber 7e into the small chamber 7f through the opened weak seal portion 5, and thereafter, the small chamber 7e is again pressed so as to mix the infusion solution therein with the infusion solution contained in the small chamber 7g by flowing the first mixed infusion solution in the small chamber 7e into the small chamber 7g to thereby mix all the infusion solutions in the chambers 7e, 7f and 7g. According to this structure, the direct mixing between the infusion solutions in the small chambers 7f and 7g can be prevented, and it is not necessary to form any weak seal portion between the small chambers 7f and 7g because the infusion solutions in these chambers are mixed through the small chamber 7e. Further, if the infusion solution bag 1C is formed so that the sealing strengths between the weak seal portions of the small chambers 7f and 7g is different, the above mentioned mixing will be more accurately performed.

As mentioned above according to the present invention, the infusion solution bag provided with a plurality of small chambers into which the infusion solutions and/or medicaments are accommodated respectively and which have the weak seal portions closed with suitable sealing strength to be easily separable can be effectively manufactured. Furthermore, the sealing strength of the weak seal portions can be optionally adjusted finely in accordance with the requirements to be used, and the thus manufactured product infusion solution bags provide uniform sealing strength.

Still furthermore, according to the present invention, since the small chambers can be formed so as to have optional shapes at desired positions, the mixing of the inner contents of the respective small chambers can be correctly performed.

It is to be noted that the present invention is not limited to the described embodiments and many other changes and modifications may be made without departing from the scopes of the appended claims.

What is claimed is:

1. An infusion bag comprising:
    a front wall portion and a back wall portion each formed of a flexible plastic film and provided with a plurality of chambers;
    a boundary portion sectioning said chambers, said boundary portion having at least one weak seal portion which is closed by separably bonding inside surfaces of the front and back wall portions mutually facing at the boundary portion so that the plural chambers are in communication when the one weak seal portion is opened; and
    a region of patterned dots of separable coating material which region of patterned dots at least occupies said one weak seal portion, the separable coating material providing a reduced bonding strength and areas of the one weak seal portion apart from each of the patterned dots being free of separable coating material,
    wherein said region of separable coating material in the form of patterned dots extends beyond said one weak seal portion on at least one of said back and front wall portions and wherein said region of separable coating material extending beyond said one weak seal portion is an unbonded region of said back and front wall portions.

2. The infusion bag of claim 1, wherein said region of separable coating material in the form of patterned dots comprises a first and second sub-region with different dot densities.

3. An infusion bag comprising:

a front wall portion and a back wall portion each formed of a flexible plastic film and provided with a plurality of chambers;

a boundary portion sectioning said chambers, said boundary portion having at least one weak seal portion which is closed by separably bonding inside surfaces of the front and back wall portions mutually facing at the boundary portion so that the plural chambers are in communication when the one weak seal portion is opened; and a region of patterned dots of separable coating material which region of patterned dots at least occupies said one weak seal portion, the separable coating material providing a reduced bonding strength and areas of the one weak seal portion apart from each of the patterned dots being free of separable coating material, wherein said region of separable coating material in the form of patterned dots comprises a first and second sub-region with different dot densities.

* * * * *